(12) United States Patent
Slezak et al.

(10) Patent No.: US 8,264,241 B2
(45) Date of Patent: Sep. 11, 2012

(54) DEVICE AND METHOD FOR MEASURING AN ELECTRICAL PROPERTY OF A FLUID FLOWING THROUGH A PIPE

(75) Inventors: Marian Jozef Walter Slezak, Rijsbergen (NL); Cornelis Wijnand Petrus Schoenmakers, Dordrecht (NL)

(73) Assignee: Fluid Well Instruments, B.V. (NL)

( * ) Notice: Subject to any disclaimer, the term of this patent is extended or adjusted under 35 U.S.C. 154(b) by 493 days.

(21) Appl. No.: 12/428,765

(22) Filed: Apr. 23, 2009

(65) Prior Publication Data
US 2009/0267619 A1 Oct. 29, 2009

(30) Foreign Application Priority Data
Apr. 25, 2008 (NL) ...................................... 2001521

(51) Int. Cl.
*G01R 27/26* (2006.01)
*G01R 27/08* (2006.01)
(52) U.S. Cl. ........................................ 324/658; 324/691
(58) Field of Classification Search .................... 324/658
See application file for complete search history.

(56) References Cited

U.S. PATENT DOCUMENTS

| 4,136,564 | A | * | 1/1979 | Suzuki et al. | ............... | 73/861.09 |
| 4,634,982 | A | * | 1/1987 | Pungor et al. | ................ | 324/448 |
| 5,068,617 | A |   | 11/1991 | Reich |   |   |
| 5,351,554 | A | * | 10/1994 | Budmiger | ................ | 73/861.17 |
| 6,655,221 | B1 | * | 12/2003 | Aspelund et al. | .......... | 73/861.04 |
| 6,865,956 | B2 | * | 3/2005 | Yamamoto | ................ | 73/861.12 |
| 7,343,820 | B2 | * | 3/2008 | Gysling et al. | ............. | 73/861.23 |
| 2008/0148867 | A1 | * | 6/2008 | Nyfors | ........................ | 73/861.63 |

FOREIGN PATENT DOCUMENTS

| DE | 2436344 | | 4/1976 |
| EP | 0819938 | A2 | 1/1998 |
| GB | 1312888 | | 4/1973 |

OTHER PUBLICATIONS

Kaj Iwansson, "NL Patent Application No. NL 2001521 Search Report and Written Opinion", Dec. 2, 2008, Publisher: Octrooicentrum Nederland, Published in: NL.

* cited by examiner

*Primary Examiner* — Jeff Natalini
(74) *Attorney, Agent, or Firm* — Kaplan Breyer Schwarz & Ottesen LLP

(57) ABSTRACT

The invention relates to a device and a method for measuring an electrical property of fluid flowing through a pipe, comprising at least a first measuring electrode and a second measuring electrode placed in spatial contact with the pipe, wherein the first measuring electrode is received in a body placed inside the inner wall of the pipe, and the first measuring electrode is separated from the inner wall of the pipe by a gap, this gap extending over at least a part of the periphery of the inner wall of the pipe. As a result of these measures the distance between the measuring electrodes is greatly reduced, so that the measurement accuracy increases considerably. The measuring circuit is preferably adapted for repeated successive measurement of the resistance value and the capacitance of the fluid.

19 Claims, 2 Drawing Sheets

DEVICE AND METHOD FOR MEASURING AN ELECTRICAL PROPERTY OF A FLUID FLOWING THROUGH A PIPE

FIELD OF INVENTION

The invention relates to a device for measuring an electrical property of fluid flowing through a pipe, comprising at least a first measuring electrode and a second measuring electrode placed in spatial contact with the pipe.

BACKGROUND OF THE INVENTION

Devices and methods for measuring an electrical property of fluid flowing through a pipe are generally known.

In such prior art measuring devices use is made of measuring electrodes received in the pipe wall so that the flow of the fluid through the pipe is affected as little as possible. This has the result that the measuring electrodes extend in an arc, so that the electric field is highly inhomogeneous and the measurement accuracy is limited. It is however possible to use straight measuring electrodes, although the distance between the electrodes then becomes greater, whereby the accuracy of the measurement likewise deteriorates.

SUMMARY OF THE INVENTION

An object of the invention is to provide such a device wherein the drawbacks are obviated.

This object is achieved in that the first measuring electrode is received in a body placed inside the inner wall of the pipe, and in that the first measuring electrode is separated from the inner wall of the pipe by a gap, this gap extending over at least a part of the periphery of the inner wall of the pipe.

As a result of these measures the distance between the measuring electrodes is greatly reduced, so that the measurement accuracy increases considerably. The centrally arranged body further has only a limited influence on the flow of the medium.

The invention likewise relates to a method for measuring an electrical property of fluid flowing through a pipe, comprising of measuring the electrical material property between a first measuring electrode and a second measuring electrode placed in spatial contact with the pipe, wherein the measurement is performed over a gap between the inner wall of the pipe and a body placed in the pipe and extending over at least a part of the periphery of the inner wall of the pipe.

According to a first preferred embodiment, the pipe has a circular internal cross-section, the body is placed concentrically in the pipe and the body is at least partially circularly symmetrical relative to the concentric axis. As a result of these measures the electric field is more rotation-symmetrical, which increases accuracy.

Although other circularly symmetrical shapes, such as cylindrical shapes, are not precluded, it is recommended that the body has an at least partially conical form.

Because the device according to the invention is suitable for measuring electrical properties of a flowing medium, there is usually also a need to measure other quantities, such as the flow speed. It is known for this purpose to make use of a local reduction in the size of the passage and a pressure difference meter for measuring the pressure difference upstream and downstream of the size-reduction, wherein the pressure difference is a measure for the flow speed. The body arranged in the pipe can then also be used as the passage-reducing body. A further embodiment therefore provides the measure that a pressure meter is placed in the pipe upstream and downstream of the body.

The body is preferably connected by means of a rod extending in axial direction to a holder extending in the radial direction of the cone and connected to the pipe wall, this resulting in a structurally attractive solution.

For the purpose of performing a measurement of the electrical properties it is attractive that the first measuring electrode is placed on the outer side of the body placed in the pipe. This is because the distances between the electrodes are hereby reduced.

In order to make the distances as small as possible, it is important that the second measuring electrode lies as close as possible to the first one. For this reason it is important to place the second measuring electrode at the position of the body placed in the pipe. In order to prevent a further narrowing of the passage occurring, and the fluid encountering more resistance during flow, it is recommended that the second measuring electrode is placed in a recess arranged in the interior pipe wall and extending all the way round, that the pipe is manufactured from electrically conductive material and that the second measuring electrode is separated from the pipe by an electrically insulating layer. This provides the option of determining the potential on the pipe independently of that on the second measuring electrode. The invention likewise relates to a method wherein the electrical capacitance of the fluid flowing through the pipe is measured with a second measuring electrode electrically separated from the interior of the pipe and received in the pipe wall.

In many cases a fluid with a good conductivity flows through the pipe. In order to then also enable the dielectric constant of this fluid to be measured without the current caused by conduction adversely affecting the measurement, it is attractive that the second measuring electrode is separated from the interior of the pipe by an electrically insulating layer.

The second measuring electrode preferably extends through an arc that is smaller than 360°, for instance through an arc of 270°. It hereby becomes possible to measure only a sector-shaped part of the cross-section, which can be of particular importance in the case of non-homogeneous fluids.

Metallic contact between the two measuring electrodes and the fluid is essential for the purpose of measuring the conductivity of the fluid flowing through the pipe. The second measuring electrode is electrically insulated. In order to still be able to measure the electrical conductivity it is attractive that the pipe is adapted to function as third measuring electrode.

For the purpose of performing the measurement of the electrical conductivity of the fluid, the device comprises a measuring circuit which is adapted to measure the electrical conductivity of the fluid between the first measuring electrode and the third measuring electrode, and which is connected to the first measuring electrode and to the third measuring electrode.

For the purpose of performing the measurement of the dielectric constant of the fluid, the device comprises a measuring circuit which is adapted to measure the capacitance of the fluid between the first measuring electrode and the second measuring electrode, and which is connected to the first measuring electrode and to the second measuring electrode.

In order to obtain more measurement data, it is attractive that the measuring circuit is adapted to successively measure the electrical conductivity and the capacitance of the fluid flowing through the pipe.

In order to avoid as far as possible the influence of parasitic capacitances and thereby increase accuracy, a preferred embodiment provides the measure that the measuring circuit is adapted to apply a voltage to the first measuring electrode and to maintain the second measuring electrode at a virtual zero point during measurement of the capacitance of the fluid between the first measuring electrode and the second measuring electrode. This measurement makes it possible to still allow accurate measurement, particularly in the case of small capacitances, i.e. in fluids with a low value of the dielectric constant. In such a situation the parasitic capacitance could after all have a much higher value than the capacitance to be measured.

The fluids usually have greater dielectric constants however, so that the capacitance values to be measured are greater and possible capacitance values are less disruptive. For such situations it can be attractive when a voltage is applied to the second measuring electrode and the first measuring electrode is earthed during measurement of the capacitance of the fluid between the first measuring electrode and the second measuring electrode. Such a high value of the dielectric constant is usually associated with a high electric conductivity. If the electrode configuration is maintained wherein the measuring voltage is applied to the first electrode and the second electrode is earthed, the high electrical conductivity would in such a situation disrupt the electric field, this to an extent such that a useful measurement of the capacitance value is no longer possible. This drawback is avoided by the measures according to the present embodiment because the second electrode is insulated and because the electric field is such that the electrically conductive components have less influence on the measured capacitance value. The greater parasitic capacitance value is tolerated here.

In order to obtain a large amount of measurement information, it is attractive to perform multiple types of capacitive measurement; measurements of the first type are after all mainly suitable for measuring low capacitance values and those of the other type mainly for high capacitance values. A further preferred embodiment therefore provides the measure that the measuring circuit is adapted to successively measure the capacitance of the fluid flowing through the pipe when a voltage is applied to the first measuring electrode and the second measuring electrode is maintained at a virtual zero point, and to measure this capacitance when a voltage is applied to the second measuring electrode and the first measuring electrode is earthed.

The realization of the measuring circuit is greatly simplified when the measuring circuit is provided with an oscillator and a selector circuit, and the selector circuit is adapted as frequency-determining element in the oscillator to switch the capacitance or resistance to be measured.

Because the composition of the fluid can vary greatly within a short period of time, it is attractive that the measuring circuit is adapted for repeated successive measurement of the resistance value and the capacitance of the fluid. This advantage is likewise obtained by a method wherein the resistance value and the capacitance of the fluid are repeatedly measured in succession.

BRIEF DESCRIPTION OF THE DRAWINGS

The invention is elucidated hereinbelow with reference to the accompanying drawings, in which.

DETAILED DESCRIPTION

Figure 1:
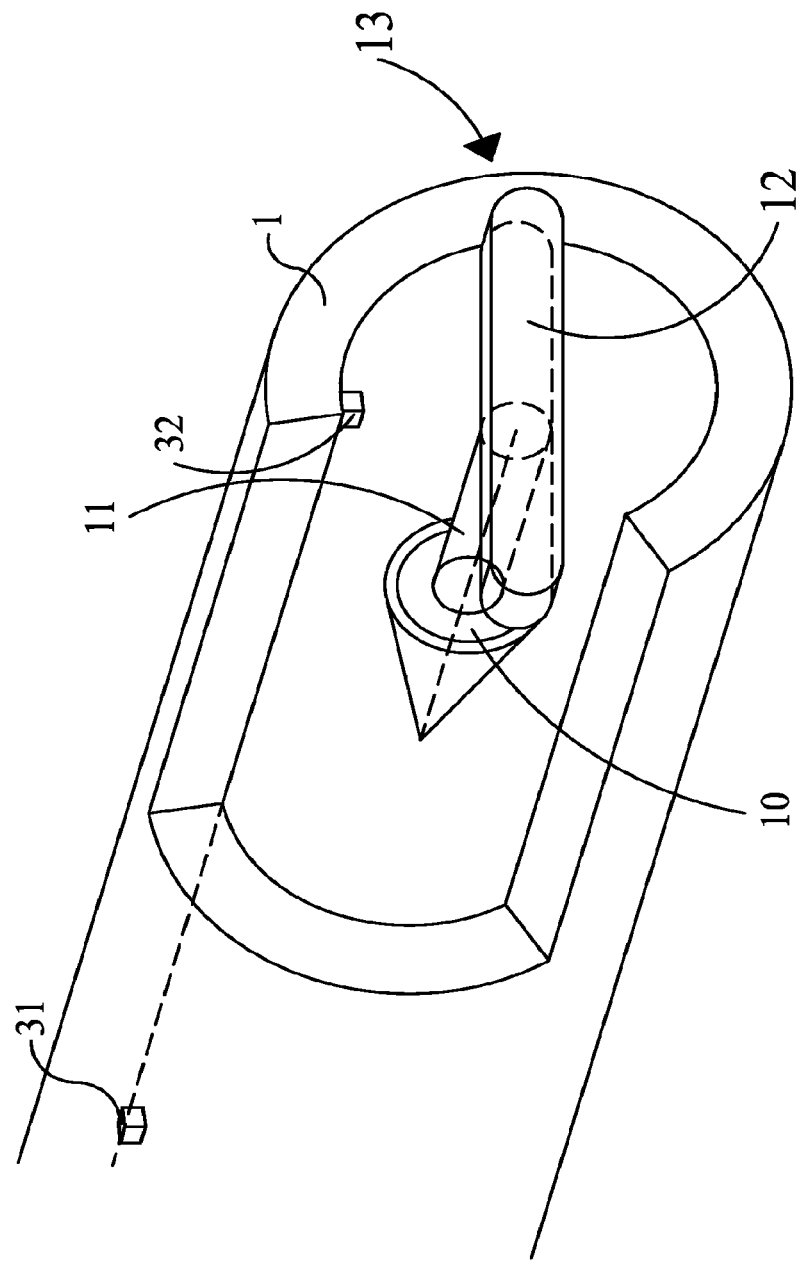
FIG. 1 is a partly cut-away schematic perspective view of a pipe piece in which the invention is implemented.
Figure 2:
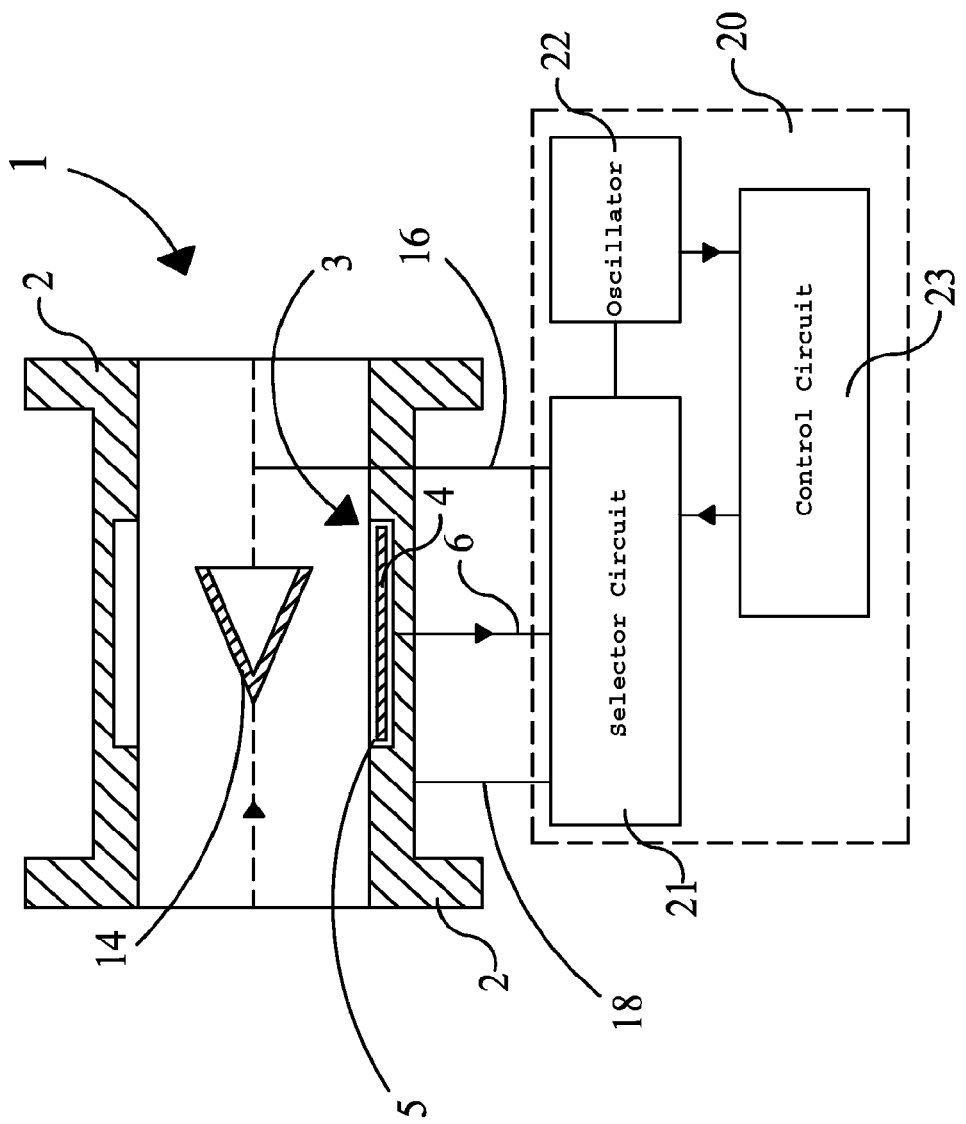
FIG. 2 is a schematic cross-sectional view of the pipe piece shown in FIG. 1, together with external components of the invention.

FIGS. 1 and 2 show a cylindrical pipe piece 1 which, as FIG. 2 shows, is provided on either side with coupling flanges 2 and which is manufactured from metal or other electrically conductive material. An annular recess 3 extending all the way round is arranged in the inner surface of the pipe piece. A curved metal measuring electrode 4 extending through an arc of less than 360°, for instance 270°, is placed in this annular recess 3. Measuring electrode 4 has a smaller width than recess 3. The cylinder encircling measuring electrode 4 also has a smaller external diameter than recess 3 and has a larger internal diameter than the internal diameter of pipe piece 1. Measuring electrode 4 can thus be placed concentrically with pipe piece 1 into recess 3 of pipe piece 1. The metal measuring electrode 4 is fixed in this position because it is enclosed by a layer 5 of electrically insulating material, such as a plastic, for instance a moulding resin. This layer 5 fully encloses the metal measuring electrode so that measuring electrode 4 is electrically insulated relative to pipe piece 1 and the interior of pipe piece 1. This measuring electrode functioning as second measuring electrode 4 is connected by means of a connecting wire 6 to a measuring circuit to be elucidated hereinbelow.

A substantially conical body 10 is further placed in the interior of pipe piece 1 concentrically thereto. Conical body 10 is connected on its end surface to a cylindrical rod 11 also extending concentrically. At its end remote from conical body 10 rod 11 is connected to a transversely extending carrier 12 which extends at both its ends into recesses 13 arranged in the inner wall of pipe piece 1. The combination of conical body 10, rod 11 and carrier 12 is preferably manufactured here from electrically insulating material such as plastic. In order to be able to fulfil its function as measuring electrode the outer surface of the conical body is provided with a layer 14 of electrically conductive material, for instance of stainless steel. This layer functions as first measuring electrode 14. It is otherwise also possible to manufacture other parts, such as rod 11 and the carrier, from electrically conductive material, although an electrically insulating element will then have to be placed at another location between the electrode and the pipe body. This measuring electrode 14 is also connected to the measuring circuit by means of a connecting wire 16 extending through rod 11 and carrier 12.

The device according to the invention is provided with a measuring circuit designated as a whole with 20. This measuring circuit 20 comprises a selector circuit 21 which is connected to the centrally arranged first measuring electrode 14 and to second measuring electrode 4 by respective connecting wires 16 and 6. Selector circuit 21 is further connected by means of a connecting wire 18 to pipe piece 1, which in some measurements also functions as measuring electrode, namely as third measuring electrode. Measuring circuit 20 also comprises an oscillator 22 and a control circuit 23.

The operation of the above stated device will now be described. Pipe piece 1 is incorporated in a pipe for guiding a fluid, such as a mixture of gases and/or liquids. An important field of application of the invention lies in oil extraction. The liquid coming out of an oil well is formed by a mixture of oil, water, usually other liquids, and sometimes gases. Such a fluid usually also comprises entrained contaminants such as sand. In order to control the process of separating these substances as well as possible, it is desirable to determine the composition of the fluid. The invention makes a contribution here by measuring the electrical conductivity and the dielectric constant of the fluid. The composition of the fluid, such as the content of oil and water, can be determined on the basis of these properties. Use is made here of the fact that water has a high dielectric constant in the order of magnitude of 80, and that oil has a dielectric constant in the order of magnitude of 2, and of the fact that oil is a good electrical insulator and water, particularly when it is contaminated with salts, is a good electrical conductor.

The device is therefore adapted to measure the electrical conductivity of the fluid flowing through pipe piece 1. Use is made for this purpose of the centrally placed first electrode 14 and the pipe 1 functioning as third electrode. The use of second electrode 4 is not possible because it is electrically insulated relative to the interior of pipe piece 1. Selector circuit 21 therefore selects connecting wires 16 and 18 for the purpose of connecting the first measuring electrode 14 and the third measuring electrode in the form of pipe piece 1 to oscillator 22. These measuring electrodes 14, 1 and the fluid present therebetween are hereby included in the frequency-determining loop of oscillator circuit 22. The circuit of oscillator 22 is such that the electrical resistance of the fluid between these electrodes determines the frequency of the oscillator. This frequency hereby forms a measure for the specific resistance of the fluid.

The device is also adapted to measure the dielectric constant of the fluid flowing through pipe piece 1. Use is made for this purpose of the centrally placed first measuring electrode 14 and second measuring electrode 4.

Use can be made of two different measuring configurations for the purpose of measuring respectively the capacitance and the dielectric constant of the fluid. According to the first configuration, a voltage is applied to the first centrally placed measuring electrode 14 and the voltage on the second measuring electrode is maintained at a virtual zero point. Selector circuit 21 therefore selects connecting wires 16 and 6 for connecting first measuring electrode 14 and second measuring electrode 4 to oscillator 22. These measuring electrodes 14, 4 and the fluid present therebetween are hereby included in the oscillator circuit, which in the present case is provided with an operational amplifier for creating a virtual zero point. The circuit of the oscillator is such that the capacitance of the two electrodes with the fluid present therebetween determines the frequency of the oscillator. This frequency hereby forms a measure for the dielectric constant of the fluid. As a result of this configuration the influence of parasitic capacitances is minimal, so that this measuring configuration is highly suitable for measuring low capacitances and fluids with low dielectric constants. Pipe piece 1 is here earthed via connecting wire 18 and selector circuit 21 in order to shield the measuring zone as much as possible from outside influences.

In some cases this capacitance lies within a wider range, depending of course on the fluid, wherein the capacitance may be determined somewhat less accurately. In such a case the first measuring electrode can be earthed and a measuring voltage can be applied to the second measuring electrode, this of course while maintaining its position inside the oscillator. The then occurring distribution of the electric field is less sensitive to the high electrical conductivity usually associated with high dielectric constants. Pipe piece 1 is also earthed in this measuring configuration.

The circuit configuration thus provides three options for performing a measurement, i.e. with the capacitance or the resistance incorporated in an oscillator circuit. In order to control the measuring process use is made of control circuit 23, which is for instance provided with a microprocessor. This control circuit is for instance adapted to successively perform a measurement of the electrical conductivity or resistance and to then perform a measurement of the capacitance or dielectric constant.

As already stated, an important field of application of the measuring method and device lies in determining the water content of mineral oil pumped up from oil wells, wherein use is made of the fact that the dielectric constant of water is several tens times greater than that of oil. Three measurements can thus be performed, such as a capacitance measurement wherein the voltage is applied to the central electrode and wherein the second electrode is (virtually) earthed, this being particularly suitable for fluids with a low capacitance value, i.e. a mixture with a low water content, for instance less than 10%. A measurement can also be performed in the alternative measuring configuration, which is particularly suitable for measurements at a somewhat higher water content, for instance between 10% and 80%, wherein the conductivity of the water already plays a part, and finally a conductivity measurement for mixtures with a high water content, for instance more than 80%.

It is possible to perform these measurements repeatedly in quick succession and with a high frequency. In general, only one of the three performed measurements will herein produce a useful result. It can therefore be attractive to perform only the measurements producing a useful result, for instance by performing a measurement associated with a different measuring range only when a trend points to this measuring range.

Because the fluid also flows through the pipe at a usually high speed, it is important to repeat the measurement quickly in order to enable detection of rapid changes in the composition of the fluid and to be able to anticipate them.

The control circuit is also adapted to transmit the measurement results to for instance a more centrally located circuit for collecting and processing measurement data.

As already stated in the preamble, the presence of the centrally arranged body 10 provides the option of measuring the pressure in the fluid by means of the pressure difference upstream and downstream of body 10 and of hereby determining the flow speed of the fluid, and thereby the flow rate thereof. Arranged for this purpose against the inner wall of pipe 1 are a first pressure meter 31, upstream of body 10, and a second pressure meter 32, downstream of body 10, both these meters being connected to control circuit 23 by means of a connecting wire shown in the drawings. Using these signals the pressure difference over body 10 is measured and the flow rate can be calculated.

It will be apparent that within the scope of the invention diverse modifications can be made to the above elucidated embodiment.

What is claimed is:

1. A device for measuring an electrical property of fluid flowing through a pipe, comprising:
   at least a first measuring electrode and a second measuring electrode placed in spatial contact with the pipe;
   wherein the first measuring electrode is received in a body placed inside the inner wall of the pipe, and being separated from the inner wall of the pipe by a gap, the gap extending over at least a part of the periphery of the inner wall of the pipe; and
   a measuring circuit adapted to:
   i) measure a capacitance of the fluid between the first measuring electrode and the second measuring electrode, the measuring circuit being connected to the first measuring electrode and to the second measuring electrode, and
   ii) measure an electrical conductivity of the fluid between the first measuring electrode and the pipe, the pipe being adapted to function as a third measuring electrode, and the measuring circuit being connected to the first measuring electrode and the third measuring electrode.

2. The device as claimed in claim 1, wherein the pipe has a circular internal cross-section, that the body is placed concentrically in the pipe and that the body is circularly symmetrical.

3. The device as claimed in claim 2, wherein the body has an at least partially conical form.

4. The device as claimed in claim 3, wherein a pressure meter is placed in the pipe upstream as well as downstream of the body.

5. The device as claimed in claim 1, wherein the body is connected by means of a rod extending in axial direction to a holder extending in the radial direction of the cone and connected to the pipe wall.

6. The device as claimed in claim 1, wherein the first measuring electrode is placed on the outer side of the body placed in the pipe.

7. The device as claimed in claim 6, wherein the second measuring electrode extends through an arc that is smaller than 360°.

8. The device as claimed in claim 1, wherein the second measuring electrode is placed in a recess arranged in the interior pipe wall and extending all the way round, and that the pipe is manufactured from electrically conductive material and that the second measuring electrode is separated from the pipe by an electrically insulating layer.

9. The device as claimed in claim 8, wherein the second measuring electrode is separated from the interior of the pipe by an electrically insulating layer.

10. The device as claimed in claim 1, wherein the measuring circuit is adapted to successively measure the electrical conductivity and the capacitance of the fluid flowing through the pipe.

11. The device as claimed in claim 1, wherein the measuring circuit is adapted to apply a voltage to the first measuring electrode and to maintain the second measuring electrode at a virtual zero point during measurement of the capacitance of the fluid between the first measuring electrode and the second measuring electrode.

12. The device as claimed in claim 1, wherein the measuring circuit is adapted to apply a voltage to the second measuring electrode and to earth the first measuring electrode during measurement of the capacitance of the fluid between the first measuring electrode and the second measuring electrode.

13. The device as claimed in claim 12, wherein the measuring circuit is adapted to successively measure the capacitance of the fluid flowing through the pipe when a voltage is applied to the first measuring electrode and the second measuring electrode is maintained at a virtual zero point and to measure this capacitance when a voltage is applied to the second measuring electrode and the first measuring electrode is earthed.

14. The device as claimed in claim 1 wherein the measuring circuit is provided with an oscillator and a selector circuit, and that the selector circuit is adapted as frequency-determining element in the oscillator to switch the capacitance or a resistance to be measured.

15. The device as claimed in claim 1, wherein the measuring circuit is adapted for repeated successive measurement of a resistance and the capacitance of the fluid.

16. A method for measuring an electrical property of fluid flowing through a pipe, comprising:
measuring an electrical capacitance of the fluid between a first measuring electrode and a second measuring electrode placed in spatial contact with the pipe, wherein the measurement of the electrical capacitance is performed over a gap between the inner wall of the pipe and a body placed in the pipe and extending over at least a part of the periphery of the inner wall of the pipe; and
measuring an electrical conductivity of the fluid between the first measuring electrode and the pipe, wherein the measurement of the electrical conductivity is performed between the pipe and the body in which the first measuring electrode is placed, and wherein the pipe is adapted to function as a third measuring electrode.

17. The method as claimed in claim 16, wherein the electrical capacitance of the fluid flowing through the pipe is measured with the second measuring electrode electrically separated from the interior of the pipe and received in the pipe wall.

18. The method as claimed in claim 17, wherein the electrical capacitance of the fluid flowing through the pipe is measured alternately with voltage applied to the first measuring electrode and the second measuring electrode being maintained at a virtual zero point, and wherein the electrical capacitance is measured when voltage is applied to the second measuring electrode and the first measuring electrode is earthed.

19. The method as claimed in claim 16, further comprising repeatedly measuring successively a resistance and the electrical capacitance of the fluid.

* * * * *